US011208426B2

(12) United States Patent
Wadhwani et al.

(10) Patent No.: US 11,208,426 B2
(45) Date of Patent: Dec. 28, 2021

(54) LACTOBIONIC ACID PRODUCTION METHODS AND PRODUCTS

(71) Applicant: Leprino Foods Company, Denver, CO (US)

(72) Inventors: Ranjeeta Wadhwani, Menasha, WI (US); Richard K. Merrill, Highlands Ranch, CO (US); Jiancai Li, Englewood, CO (US)

(73) Assignee: Leprino Foods Company, Denver, CO (US)

( * ) Notice: Subject to any disclaimer, the term of this patent is extended or adjusted under 35 U.S.C. 154(b) by 226 days.

(21) Appl. No.: 16/259,810

(22) Filed: Jan. 28, 2019

(65) Prior Publication Data

US 2020/0239511 A1 Jul. 30, 2020

(51) Int. Cl.
  *C07H 15/04* (2006.01)
  *B01D 61/44* (2006.01)
  *C12P 19/02* (2006.01)

(52) U.S. Cl.
  CPC ............ *C07H 15/04* (2013.01); *B01D 61/445* (2013.01); *C12P 19/02* (2013.01); *C12Y 101/03009* (2013.01)

(58) Field of Classification Search
  None
  See application file for complete search history.

(56) References Cited

U.S. PATENT DOCUMENTS

| 5,198,086 A | 3/1993 | Chlanda et al. |
| 2002/0006884 A1 | 1/2002 | Jones et al. |
| 2007/0154595 A1 | 7/2007 | Budtz et al. |

OTHER PUBLICATIONS

Peretti, FA; et al; "Use of electrodialysis technique for the separation oflactobionic acid produced by Zymomonas mobilis" Desalination, 245, 626-630, 2009 (Year: 2009).*
Bailly, Mathieu; "Production of organic acids by bipolar electrodialysis: realizations and perspectives" Desalination, 144, 157-162, 2002 (Year: 2002).*

(Continued)

*Primary Examiner* — David W Berke-Schlessel
(74) *Attorney, Agent, or Firm* — Kilpatrick Townsend & Stockton, LLP

(57) ABSTRACT

Systems and methods of making lactobionic acid are described. The systems include two-compartment cation bipolar electrodialysis assemblies having at least one cell that includes a cation ion-exchange membrane and a bipolar membrane. The membranes define the borders of a pair of flow channels for a separate (i) caustic stream and (i) purified lactobionic acid stream. Lactobionate ions in the lactobionic acid stream do not cross a membrane in the electrodialysis assembly, which reduces membrane fouling. The methods include passing a lactobionate salt through a two-compartment cation bipolar electrodialysis assembly. The electrodialysis assembly includes at least one two-compartment cation bipolar membrane cell, and separates the lactobionate salt into a caustic compound and the lactobionic acid. The assembly is designed so the lactobionate ions do not cross an ion exchange membrane in the assembly to form the lactobionic acid, which reduces membrane fouling.

22 Claims, 8 Drawing Sheets

Two Compartment Cation Bipolar ED 200

(56) References Cited

OTHER PUBLICATIONS

Gutierrez, et al., "Production of Lactobionic Acid by Means of a Process Comprising the Catalytic Oxidation of Lactose and Bipolar Membrane Electrodialysis", Separation and Purficataion Technology, Feb. 19, 2013, pp. 23-32.

PCT/US2020/015299 received an international Search Repost and Written Opinion dated April 9, 2020, 10 pages.

* cited by examiner

LACTOBIONIC ACID PRODUCTION METHODS AND PRODUCTS

BACKGROUND

Lactobionic acid (LBA) is a commercially valuable product that can be made from the sugar lactose, which is naturally found in the milk of cows and other animals. Unfortunately, lactose is difficult to digest for many people, and a growing market has developed for dairy products where some or all of the lactose has been removed. These products include lactose-free milk, ice cream, and cheese, among other foods. As demand increases for lactose-reduced and lactose-free products, the question of what to do with the low-value lactose becomes increasingly urgent. For many producers, lactose has shifted from a commodity to an expense with regularly increasing disposal costs. Producers typically pass these costs on to the consumers of their lactose-free products.

Instead of relegating lactose to low value uses such as incorporation into animal feed, or disposal in landfills, converting lactose to lactobionic acid can turn a burdensome by-product into a valuable commodity. However, that conversion only makes economic sense when the cost of conversion is less than the value of the lactobionic acid, and a significant percentage of the conversion costs is getting the lactobionic acid to the requisite level of purity, including the reduction of residual levels of lactose in the lactobionic acid. Reducing those conversion costs continues to be a challenge for the industry.

Processes have been developed to convert lactose to lactobionic acid using chemical reactants, biologically-derived enzymes, and inorganic catalysts. In most of these processes, the conversion from lactose to a lactobionate product proceeds most efficiently in an alkaline reaction medium. Since the aldobionate products are acidic, alkaline buffers are often used to keep the pH of the reaction medium at a threshold level or higher. For lactobionic acid destined for food and medical applications, the toxicity of the buffers needs to be low, and some common buffers include ammonium, alkali metal, alkali earth metal, and metal hydroxides. Consequently, the conversion of the lactose does not produce pure lactobionic acid, but instead lactobionate salts that have the ammonium, alkali metal, alkali earth metal, or metal cation from the buffer (e.g., $NH_4^+$, $Na^+$, $K^+$, $Ca^{2+}$, $Mg^{2+}$, $Zn^{2+}$, etc.) as a conjugate cation.

The purification of the lactobionate salt to lactobionic acid has conventionally been done using ion exchange methods that exchange the conjugate cation with a hydrogen ion ($H^+$). These methods can be effective, but typically require large quantities of expensive ion exchange resins for commercial-scale production of lactobionic acid. Moreover, the resins need to be regularly recharged, producing a waste stream in the process, and can eventually reach a condition where they need to be replaced with new resin. This makes ion exchange processes expensive and environmentally unfavorable for commercial-scale production of lactobionic acid from lactobionate salts.

More recently, producers have been experimenting with electrodialysis systems to replace the conjugate cations in the lactobionate salts with hydrogen ions. These methods use a combination of electric fields and ion exchange membranes to move the conjugate cations and lactobionate anions into separate product streams. Unlike ion-exchange methods, the electrodialysis membranes do not have to be regularly replenished because the cations and anions migrate through membranes instead of staying attached to the resin.

However, membrane fouling has become a significant problem in electrodialysis methods, caused by the unwanted buildup of ion species, especially lactobionate anions, on membrane surfaces. The fouling reduces the productivity of the electrodialysis system over time, and eventually requires the cleaning and/or replacement of the membranes. The loss of productivity and disposal of irreversibly fouled membranes adds costs and environmental pollution to these electrodialysis methods. Thus, there is a desire to develop more efficient electrodialysis methods that avoid the fouling problems encountered with conventional electrodialysis methods for converting lactobionate salts to lactobionic acid. Examples of these more efficient systems and methods are described below.

BRIEF SUMMARY

Systems and methods are described for making lactobionic acid in a purified form. They include the conversion of lactose sugar to lactobionate salts using chemical and/or enzymatic reactions that facilitate the oxidation of the glucose unit of lactose to a gluconate unit. These reactions are done in aqueous mixtures or solutions that have a controlled pH through the addition of buffers. In many examples, the buffers are inorganic hydroxide and carbonate compounds that convert the nascent lactobionic acid into a lactobionate salt. For example, when potassium hydroxide is used as a buffer, the lactobionic acid quickly forms a potassium lactobionate salt in the aqueous medium.

When the oxidation reaction is completed, and most or all of the lactose is converted to lactobionate salts, the solution may be fed to a two-compartment bipolar electrodialysis assembly. The assembly is designed to remove the conjugate cations (e.g., $K^+$ ions) from the stream of lactobionate salts and replace them with hydrogen ions to convert the salt to lactobionic acid. The conjugate cations are removed without requiring the lactobionate anions to cross a membrane in the assembly, which greatly reduces downtime for cleaning and replacement of membranes that have been fouled with precipitated lactobionate products. The design of the present two-compartment bipolar electrodialysis assembly generates a purified lactobionic acid stream at much greater rates over time in operation than conventional electrodialysis assemblies.

Embodiments include methods of making lactobionic acid from a lactobionate salt by passing the lactobionate salt through an electrodialysis assembly. The electrodialysis assembly includes at least one two-compartment bipolar membrane cell and separates the lactobionate salt into a caustic compound and the lactobionic acid. The assembly is designed so the lactobionate ions do not cross an ion exchange membrane in the assembly to form the lactobionic acid.

Embodiments also include methods of making a lactobionic acid concentrate from a lactobionate salt. The methods include passing an aqueous lactobionate salt solution through an electrodialysis assembly that has at least one two-compartment bipolar membrane cell. The electrodialysis assembly separates the aqueous lactobionate salt solution into a caustic compound solution and a lactobionic acid solution. A portion of the water is evaporated from the lactobionic acid solution to form the lactobionic acid concentrate having a total solids content of at least 10%. The assembly is designed so the lactobionate ions do not cross an ion exchange membrane in the electrodialysis assembly to form the lactobionic acid solution.

Embodiments further include methods of making lactobionic acid from a lactobionate salt. The methods include converting lactose to the lactobionate salt with a lactose oxidase enzyme and filtering the lactose oxidase enzyme from the lactobionate salt. The filtration should produce a filtered lactobionate salt that includes less than 0.02 wt. %, on a dry basis, of the enzyme. The filtered lactobionate salt can then be passed through an electrodialysis assembly that includes at least one two-compartment cation bipolar membrane cell. The assembly separates the lactobionate salt into a caustic compound and the lactobionic acid. The assembly is designed so the lactobionate ions do not cross an ion exchange membrane in the electrodialysis assembly to form the lactobionic acid solution.

Still further embodiments include systems for making lactobionic acid. The systems include a two-compartment cation bipolar electrodialysis assembly made from at least one two-compartment cation bipolar electrodialysis cell. Each cell includes a bipolar membrane operable to dissociate water molecules into hydrogen ($H^+$) ions (also referred to as hydronium ions ($H_3O^+$)) and hydroxyl ions ($OH^-$). The cell also includes an ion exchange membrane. The membranes also function as partitions that define separate salt and caustic streams in the cell. Lactobionate salts are introduced to the cell through the salt stream and the salts are converted into lactobionic acid as they progress in the salt stream. The lactobionate anion portion of the lactobionate salt remains in the salt stream during the conversion and does not cross a membrane while in the cell.

Additional embodiments and features are set forth in part in the description that follows, and in part will become apparent to those skilled in the art upon examination of the specification. The features and advantages of these and other embodiments may be realized and attained by means of the instrumentalities, combinations, and methods described in the specification.

BRIEF DESCRIPTION OF THE DRAWINGS

A further understanding of the nature and advantages of selected embodiments of the invention may be realized by reference to the remaining portions of the specification and the drawings wherein like reference numerals may be used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

DETAILED DESCRIPTION

The present methods and systems for purifying lactobionic acid use a two-compartment cation bipolar electrodialysis assembly configured to reduce or eliminate membrane fouling caused by the traversal of lactobionate anions across the assembly's membranes. In both conventional electrodialysis and three-compartment bipolar membrane electrodialysis, lactobionate anions attempt to traverse at least one of the assembly's membranes and quickly clog the surface of the membranes with deposits of lactobionate salts. The membrane fouling leads to reduced output of purified lactobionic acid from the assembly, sometimes in less than one hour, and increased downtime for assembly cleaning and maintenance. The fouled membranes also need to be replaced more frequently, leading to increased expenses for the purchase of new membranes and disposal of irreversibly fouled membranes.

Conventional Electrodialysis Cells

Figure 1A:
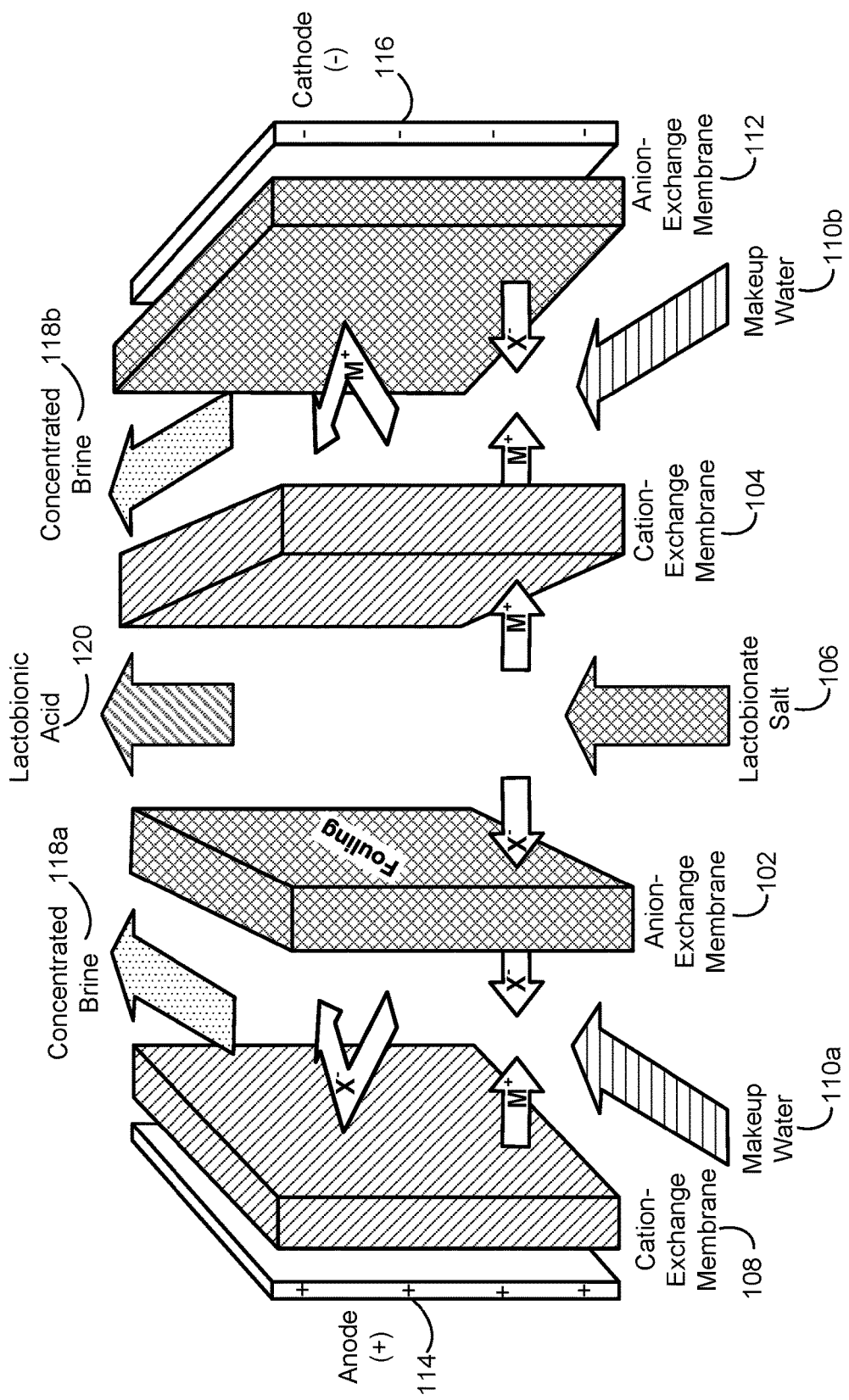
FIG. 1A is a schematic drawing of a prior art, conventional electrodialysis assembly.

An example of a conventional electrodialysis system is the conventional electrodialysis assembly shown in FIG. 1A. The cell 100 includes an anion exchange membrane 102 and a cation exchange membrane 104 arranged in parallel to define a flow channel for a lactobionate salt stream 106. A second cation exchange membrane 108 arranged adjacent to the anion exchange membrane 102 defines a flow channel for a first purified water stream 110a, while a second anion exchange membrane 112 adjacent to the cation exchange membrane 104 defines a flow channel for a second purified water stream 110b.

When the lactobionate salt stream 106 enters the assembly, the lactobionate anions ($X^-$) in the stream are coulombically attracted to the assembly's positively-charged anode electrode 114, while the salt's conjugate cations ($M^+$) are attracted to the assembly's negatively-charged cathode electrode 116. Initially, the lactobionate anions ($X^-$) in the lactobionate salt stream 106 pass through the anion exchange membrane 102 and form a lactobionate salt brine 118a with the conjugate cations ($M^+$) that pass through the second cation exchange membrane 108. At the same time, the salt's conjugate cations ($M^+$) in the lactobionate salt stream 106 pass through cation exchange membrane 104 and form another lactobionate salt brine 118b with the lactobionate anions ($X^-$) that pass through the second anion exchange membrane 112. The removal of the lactobionate anions ($X^-$) and conjugate cations ($M^+$) leaves behind a purified lactobionic acid stream 120 that exits the assembly along with the streams of lactobionate salt brine 118a-b.

The lactobionate anions ($X^-$) are large enough to adhere to exposed surfaces of the anion-exchange membranes 102, 112, without passing through the membrane. This anion buildup can quickly cause the fouling of the anion exchange membranes 102, 112, which reduces the rate at which the anions can cross the membrane. Eventually, the membranes become so fouled that anion migration effectively stops even when a highest effective voltage is applied across the assembly's electrodes. At that point, if not before, the operation of the conventional electrodialysis assembly is stopped so that the fouled membranes can be cleaned or replaced.

Figure 1B:
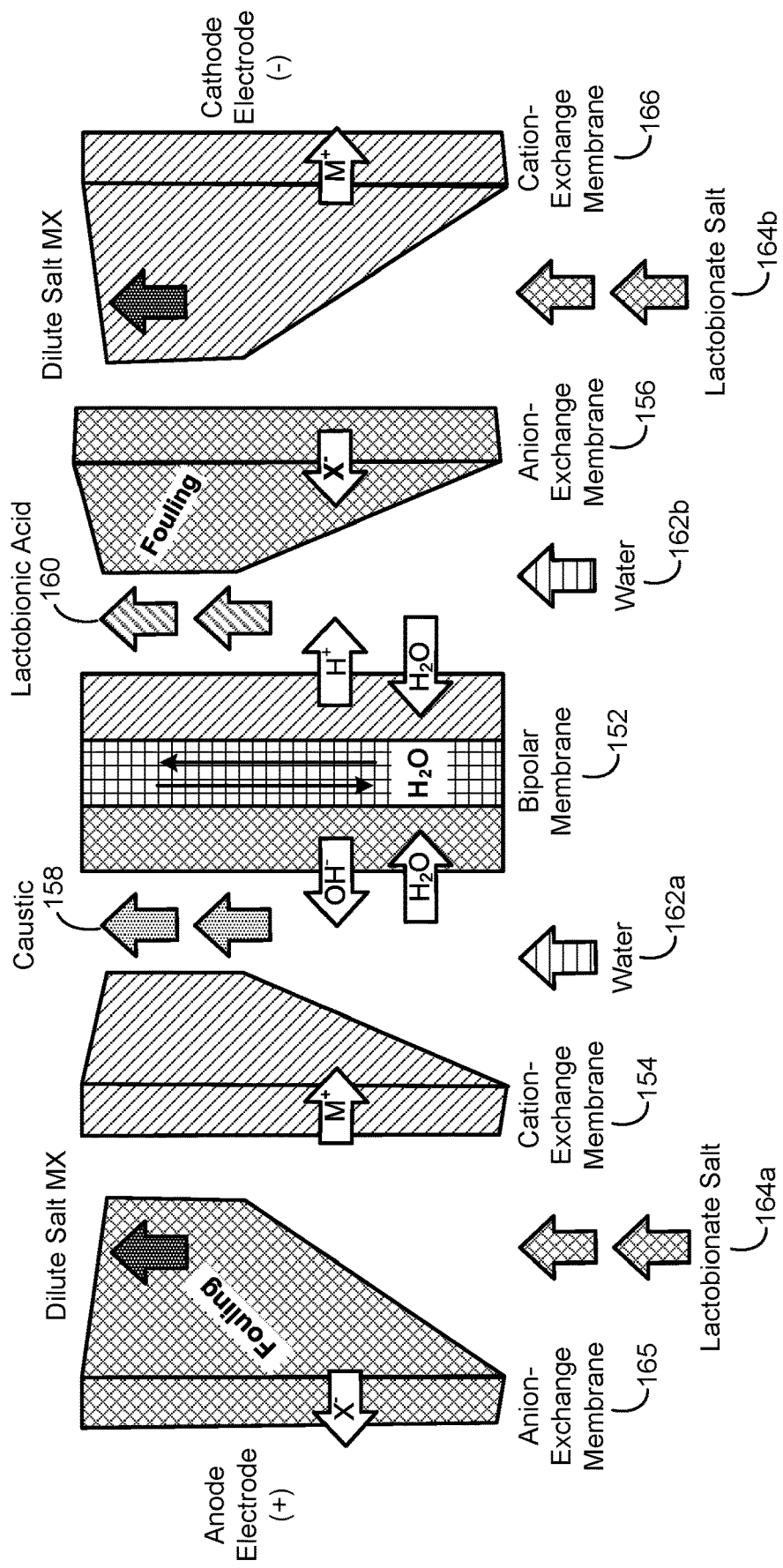
FIG. 1B is a schematic drawing of a prior art, conventional three-compartment electrodialysis assembly.

Another example of a conventional electrodialysis system is the three-compartment bipolar electrodialysis assembly shown in FIG. 1B. The cell 150 includes a bipolar membrane 152 arranged in parallel between a cation exchange membrane 154 on one side, and an anion exchange membrane 156 on the other side. A first compartment for a caustic stream 158 is formed between the bipolar membrane 152 and the cationic exchange membrane 154, while a second compartment for a stream of purified lactobionic acid 160 is formed between the bipolar membrane 152 and the anion exchange membrane 156. Purified water 162a-b is supplied to the inlets of both the first and second compartments and is split by the bipolar membrane 152 into hydrogen ions ($H^+$) and hydroxyl ions ($OH^-$). The hydrogen ions enter the purified lactobionic acid stream 160 and the hydroxyl ions ($OH—$) enter in the caustic stream 158.

In the embodiment shown in FIG. 1B, a pair of third compartments that define flow channels for a lactobionate salt streams 164a-b is formed by the cation and anion exchange membranes being paired with an opposite ion exchange membrane from an adjacent cell. Specifically, lactobionate salt stream 164a is formed by cation exchange membrane 154 being arranged opposite of an anion exchange membrane 165 from an adjacent electrodialysis cell, and lactobionate salt stream 164b is formed by anion exchange membrane 156 being arranged opposite a cation exchange membrane 166 from a different, adjacent electrodialysis cell.

In operation, the three-compartment bipolar electrodialysis assembly starts with a flow of purified water through first and second compartments, and a flow of aqueous lactobionate salt stream 164a-b through the pair of third compartments. Initially, the purified water and aqueous salt solution are pumped through the compartments without a voltage applied across the anode and cathode electrodes (not shown) of the assembly to prime the system for fluid ion exchange between the cell's ion-exchange membranes. Following the priming period, a voltage is applied across the cell from the anode and cathode electrodes to force the lactobionate anion and conjugate cation across the ion exchange membranes. Specifically, the lactobionate anions ($X^-$) in the aqueous lactobionate salt stream attempt to cross the anion exchange membrane 156 into the purified lactobionic acid stream 160, while the salt's conjugate cation ($M^+$) crosses the cation exchange membrane 154 into the caustic stream 158. Charge balance in the purified lactobionic acid stream 160 is maintained by the migration of hydrogen ($H^+$) ions from the bipolar membrane 152 into the purified lactobionic acid stream. Similarly, charge balance in the caustic stream 158 is maintained by the migration of hydroxyl ion ($OH^-$) from the bipolar membrane 152 into the caustic stream.

The negatively-charged lactobionate anions ($X^-$) are coulombically attracted to the positively-charged anode electrode, causing the anions to migrate from the aqueous lactobionate salt stream 164b through the anion exchange membrane 156 into the purified lactobionic acid stream 160. In the same aqueous lactobionate salt stream 164b, the positively-charged conjugate cations ($M^+$) migrate in the opposite direction from the lactobionate anions ($X^-$) towards the negatively-charged cathode electrode. The conjugate cations ($M^+$) migrate through the cation exchange membrane 166 into a caustic stream where they are combined with hydroxyl ions generated from an adjacent bipolar membrane. As the caustic stream 158, purified lactobionic acid stream 160, and aqueous lactobionate salt streams 164a-b, circulate through the cells of the three-compartment bipolar electrodialysis assembly, the caustic and purified lactobionic acid streams become more concentrated with caustic compound and lactobionic acid, respectively, while the aqueous lactobionate salt streams become more depleted of lactobionate salt.

FIG. 1B shows the migration of lactobionate anions ($X^-$) from the aqueous lactobionate salt stream 164b to the purified lactobionic acid stream 160 by crossing the anion-exchange membrane 156. This crossing of the lactobionate anions ($X^-$) across anion-exchange membranes occurs throughout the three-component bipolar electrodialysis cells of the assembly. The size of the lactobionate anions ($X^-$) are large enough for them to adhere in significant quantities to exposed surfaces of the anion-exchange membranes without passing through the membrane. This anion buildup can quickly cause the fouling of the anion exchange membranes, which reduces the rate at which the anions can cross the membrane. Eventually, the membranes become so fouled that anion migration effectively stops even when a highest effective voltage is applied across the assembly's electrodes. At that point, if not before, the operation of the assembly is stopped so that the fouled membranes can be cleaned or replaced.

One solution to slow the rate of membrane fouling is to increase the size of the pores in the anion exchange membranes. Larger pores increase the chances that the lactobionate anions ($X^-$) will pass through the membrane without getting stuck on exposed surfaces. However, increased pore size also makes the membrane less selective for the passage of target ions (i.e., the lactobionate anions), and permits more contaminants to move between the streams that are partitioned by the membrane. When the increase in membrane pore size is accompanied by a significant increase in the contamination of the partitioned streams, the overall rate of purification in the lactobionic acid stream can be comparable or less than the rate achievable with smaller-pored, more fouling prone, ion-exchange membranes.

The present two-compartment cation bipolar membrane design significantly reduces fouling caused by lactobionate anions without having to increase the size of the pores in the membrane. This is achieved by designing a flow stream that removes cations from the starting aqueous lactobionate salt stream while keeping the lactobionate anions in the flow stream. Because the lactobionate anions do not cross an anion-exchange membrane during the electrodialysis purification process, membrane fouling is significantly reduced or eliminated.

Exemplary Two-Compartment Cation Bipolar Electrodialysis Cells

Figure 2:
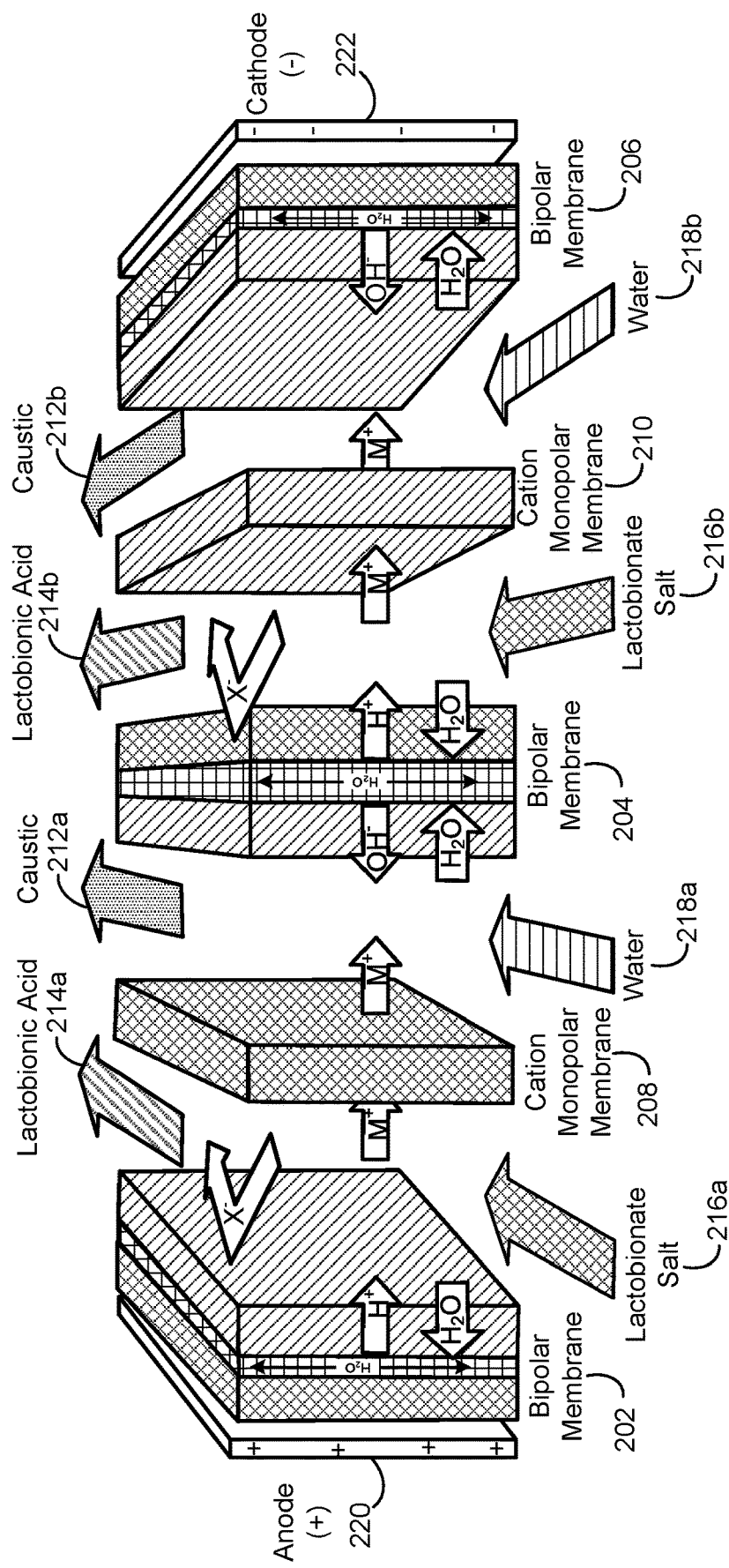
FIG. 2 is a simplified schematic drawing showing selected components of a two-compartment cation bipolar electrodialysis assembly according to embodiments of the invention.

FIG. 2 shows a simplified schematic drawing of selected components of a cell pair from a two-compartment electrodialysis assembly according to present embodiments. The cell pair 200 includes bipolar membranes 202, 204, and 206 that are separated by a pair of first and second cation exchange membranes 208 and 210. Flow channels formed (i) between the first cation exchange membrane 208 and the bipolar membrane 204 and (ii) between the second cation exchange membrane 210 and bipolar membrane 206 define compartments that output caustic streams 212a-b that include at least one caustic compound formed from the conjugate cations ($M^+$) of the starting lactobionate salt. Additional flow channels formed (i) between bipolar membrane 202 and the first cation exchange membrane 208 and (ii) between the bipolar membrane 204 and the second cation exchange membrane 210 define compartments that output purified lactobionic acid streams 214a-b formed from the lactobionate anions ($X^-$) of the starting lactobionate salt.

The two-compartment bipolar assembly further includes (i) inputs for an aqueous lactobionate salt streams 216a-b and water 218a-b, and (ii) outputs for the purified lactobionic acid streams 214a-b and caustic streams 212a-b. The inputs for the aqueous lactobionate salt streams 216a-b are fluidly connected to the compartments of the assembly that transform the solution into the purified lactobionic acid streams 214a-b as they travel through the cells of the assembly to reach the purified lactobionic acid stream output. The inputs for the water 218a-b are fluidly connected to the compartments of the assembly that split a portion of the water 218a-b into hydrogen ions and hydroxyl ions in the bipolar membranes 202, 204, and 206. The hydroxyl ions flow into cation streams and form caustic compounds, while the hydrogen ions flow into lactobionate streams and form lactobionic acid.

In operation, the two-compartment cation bipolar electrodialysis assembly starts with a flow of lactobionate salt streams 216a-b and water 218a-b through their respective compartments. Initially, both fluids are pumped through the compartments without a voltage applied across the anode electrode 220 and cathode electrode 222 of the assembly to prime the system for fluid ion exchange between the cell's membranes. Following a priming period that may last from 2-15 minutes, a voltage is applied to the cells of the assembly from the anode and cathode electrodes to force the migration of the conjugate cations ($M^+$) across the cation-exchange membranes 208 and 210. Specifically, the conjugate cations ($M^+$) originating from the lactobionate salt streams 216a-b move through the cation-exchange membranes 208 and 210 into the caustic streams 212a-b. Charge balance in the caustic streams 212a-b is maintained by the introduction of hydroxyl ions ($OH^-$), generated by the hydrolysis of water in adjacent bipolar membranes 202, 204, and 206, that form caustic hydroxide compounds (MOH) with the entering conjugate cations ($M^+$). Similarly, charge balance in the purified lactobionic acid streams 214a-b is maintained by the introduction of hydrogen ions ($H^+$), generated by the hydrolysis of water in the adjacent bipolar membranes 202, 204, and 206, that form lactobionic acid with the lactobionate anions ($X^-$) that remain in the streams.

As the conjugate cations ($M^+$) originating with the aqueous lactobionate salt streams 216a-b migrate to the caustic streams 212a-b and get replaced with hydrogen ions (H+), the purified lactobionic acid streams 214a-b of the cell pair 200 become progressively purer. Aqueous lactobionate salt streams 216a-b start with 15-50 wt. % lactobionate salt (as measured on a total solids basis) and roughly 0 wt. % lactobionic acid. Exemplary lactobionate salts include one or more of sodium lactobionate, potassium lactobionate, ammonium lactobionate, calcium lactobionate, magnesium lactobionate, and zinc lactobionate. The type of lactobionate salt depends on the alkaline buffer used during the conversion of lactose to the lactobionate salt. The two-compartment cation bipolar electrodialysis system transforms the starting aqueous lactobionate salt streams 216a-b into purified lactobionic acid streams 214a-b containing 80-97 wt. % lactobionic acid (total solids (TS) basis) output from the two-compartment cation bipolar electrodialysis assembly. Exemplary lactobionic acid concentration ranges for the output lactobionic acid streams 214a-b include up to 90 wt. % lactobionic acid (TS basis); up to 91 wt. % lactobionic acid (TS basis); up to 92 wt. % lactobionic acid (TS basis); up to 93 wt. % lactobionic acid (TS basis); up to 94 wt. % lactobionic acid (TS basis); up to 95 wt. % lactobionic acid (TS basis); up to 96 wt. % lactobionic acid (TS basis); up to 97 wt. % lactobionic acid (TS basis); 90-97 wt. % lactobionic acid (TS basis); and 95-97 wt. % lactobionic acid (TS basis), among other concentration ranges.

Unlike the electrodialysis assemblies shown in FIGS. 1A and 1B, the lactobionate anions ($X^-$) from the lactobionate salt streams 216a-b remain in the purified lactobionic acid streams 214a-b as they travel through the two-compartment bipolar electrodialysis assembly. Few lactobionate anions collect on the cation exchange membranes 208 and 210, or the bipolar membranes 202, 204, and 206 that define the walls of the purified lactobionic streams 214a-b, even after hours of operation. Thus, the lactobionate anions do not foul any of the membranes in the present two-component cation bipolar electrodialysis assembly, and do not slow the output of the purified lactobionic acid streams 214a-b over time or cause cleaning, maintenance and membrane disposal delays and expenses for the present systems.

A plurality of cells like cell pair 200 may be fluidly connected in series to create a cell stack (not shown) in the assembly. Exemplary numbers of cells arranged into a stack include 2-100 cells; 2-50 cells; 2-25 cells; 5-25 cells; and 10-20 cells, among other ranges of cells. The number of cells in the cell stack of the assembly depends in part on target purity and throughput rates for the lactobionic acid streams 214a-b traveling through the two-compartment cation bipolar electrodialysis assembly.

The output of the caustic streams 212a-b include a concentration of caustic hydroxide compound (MOH) that depends on the rate of conjugate cations ($M^+$) migrating through the cation-exchange membranes 208 and 210, as well as the flow volume of the water 218a-b supplied to the assembly. Exemplary concentration ranges for the caustic compound (MOH) in the caustic streams 212a-b include 1-5 wt. % (TS basis); 1-4 wt. % (TS basis); 1-3 wt. % (TS basis); and 1-2 wt. % (TS basis), among other ranges. Exemplary caustic compounds include one or more of sodium hydroxide (NaOH), potassium hydroxide (KOH), ammonium hydroxide ($NH_4OH$), calcium hydroxide ($Ca(OH)_2$), magnesium hydroxide ($Mg(OH)_2$), and zinc hydroxide ($Zn(OH)_2$), among other caustic compounds. The composition of the caustic compounds depends on the conjugate cation ($M^+$) in the lactobionate salt. The caustic streams 212a-b output from the assembly may be used in the alkaline buffer added to the lactose solution before or during the conversion of the lactose to lactobionate salts in the solution.

Exemplary Systems for Making Lactobionic Acid

Figure 3:
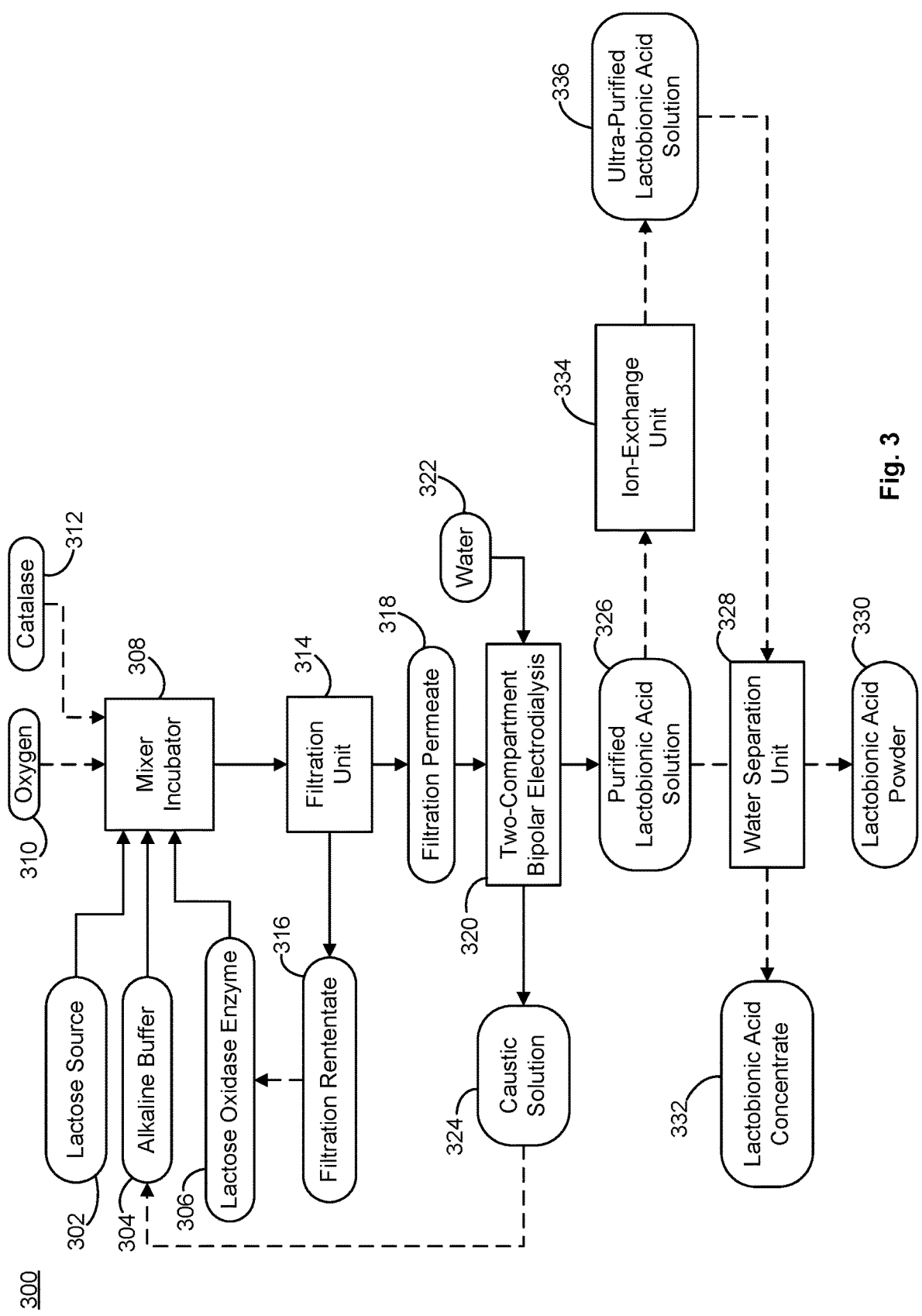
FIG. 3 is a simplified schematic drawing of a system for making a purified lactobionic acid product according to embodiments of the invention.

The exemplary cell pair 200 of the two-compartment cation bipolar electrodialysis assembly shown in FIG. 2 may be part of a larger system for making a purified lactobionic acid product like the one shown in FIG. 3. The system 300 shown in FIG. 3 includes a lactose source 302, an alkaline buffer source 304, and a lactose oxidase enzyme source 306 all feeding into a mixer/incubator 308 where the lactose is enzymatically converted into a lactobionate salt.

The lactose source 302 may be derived from dairy source such as milk, yogurt, and/or cheese, among other dairy sources. For example, the lactose source 302 may come from a yogurt or cheese-making process that generates as lactose-containing by-product. Depending on the process, the lactose-containing by-product may require further purification (e.g., filtration or crystallization) to make the lactose source 302, or the lactose-containing by-product may be used directly as the lactose source 302. Exemplary lactose sources 302 are aqueous solutions or mixtures with a lactose concentration ranging from 30-35 wt. % (TS basis).

The alkaline buffer source 304 may be a hydroxide compound in an aqueous solution. Exemplary hydroxide compounds include sodium hydroxide (NaOH), potassium hydroxide (KOH), ammonium hydroxide (NH$_4$OH), calcium hydroxide (Ca(OH)$_2$), magnesium hydroxide (Mg(OH)$_2$), and zinc hydroxide (Zn(OH)$_2$), among other hydroxide compounds. The concentration of the hydroxide compound in the aqueous solution typically ranges from 1-5 wt. % (TS basis), for example 1.2 wt. %. The quantity of the alkaline buffer source 304 added to the mixer/incubator 308 is dictated by the target pH of the combined mixture in the mixer/incubator 308. The target pH range during the conversion of lactose to the lactobionate salt ranges from 4.6 to 8, and the flow rate of the alkaline buffer source 304 into the mixer/incubator 308 may be periodically adjusted to maintain the pH within a target range (e.g., a pH range greater than 5 and less than 7) or at a target value. As noted elsewhere, the cation of the hydroxide compound (e.g., Na$^+$, K$^+$, NH$_4^+$, Ca$^{2+}$, Zn$^{2+}$) becomes the conjugate cation (M$^+$) of the lactobionate salt that is generated in the mixer/incubator 308 and subsequently purified to lactobionic acid in the two-compartment cation bipolar electrodialysis assembly 320.

The lactose oxidase enzyme source 306 may include one or more carbohydrate oxidases that are capable of enzymatically converting lactose sugar to lactobionic acid. Exemplary carbohydrate oxidases include lactose oxidases, hexose oxidases, glucose oxidases, etc., capable of enzymatically converting lactose to lactobionic acid. Exemplary carbohydrate oxidase enzymes may be derived from algae species such as *Chrondrus crispus, Iridophycus flaccidum*, and *Euthora cristata*, among other algae species. They may also be derived from fungus species such as *Microdochium nivale*, among other fungi in the *Microdochium* genus, or bacterial species such as *Acetobactor orientalis, Burkolderia cepaca*, and *Pseudomonas mucidolens*, among other bacterial species. The amount of the lactose oxidase enzyme source 306 used depends on the amount of lactose being enzymatically converted to lactobionic acid (and ultimately forming a lactobionate salt) in the combined mixture placed in the mixer/incubator 308. Exemplary amounts of lactose oxidase enzyme source 306 added to the combined mixture range from 1 to 10,000 oxidase units (OXU) per kilogram of lactose source 302, where an OXU is defined as the amount of enzyme needed to convert one µmol of lactose to lactobionic acid in one minute. Additional exemplary amounts of the lactose oxidase source 306 added to the combined mixture may include 5 to 5,000 OXU; 5 to 1,000 OXU; 5 to 500 OXU; and 5 to 100 OXU, among other ranges.

System 300 may also optionally include an oxygen source 310 and/or a catalase enzyme source 312 that becomes part of the combined mixture in the mixer/incubator 308. Both the oxygen source 310 and the catalase enzyme source 312 provide additional oxygen (O$_2$) to the carbohydrate oxidase enzymes (i.e., lactose oxidase enzymes) as they enzymatically convert lactose to lactobionic acid. The oxygen source 312 supplies O$_2$ directly in the form of air (which is about 21 vol. % O$_2$) or purified oxygen that is concentrated to a greater extent than what is found in air (e.g., greater than 80 vol. % O$_2$, greater than 90 vol. % O$_2$; greater than 95 vol. % O$_2$; greater than 99 vol. % O$_2$; etc.). The catalase source 312 indirectly supplies O$_2$ to the enzymes by taking the hydrogen peroxide product (H$_2$O$_2$) of the carbohydrate oxidase enzymatic conversion and converting it back into oxygen (O$_2$) and water. The gaseous oxygen source 310 may be supplied to the combined mixture in the mixer/incubator 308 through a bubbler, fan, and/or mixer/agitator (not shown) in the mixer/incubator 308. Exemplary flow rates for the gaseous oxygen source 310 may be set to provide a dissolved oxygen content to the combined mixture of at least 3.2 mg O$_2$/L. The catalase source 312 may be supplied to the mixer/incubator 308 based on the amount of H$_2$O$_2$ to be catalytically converted by the catalase enzymes back to oxygen and water. Exemplary amounts of the catalase source 312 added to combined mixture may range from an amount sufficient to reduce the amount of H$_2$O$_2$ in the mixture by at least 10 mol. %; at least 20 mol. %; at least 30 mol. %; at least 40 mol. %; at least 50 mol. %; at least 60 mol. %; at least 70 mol. %; at least 80 mol. %; or at least 90 mol. %, compared to the amount of H$_2$O$_2$ present in the mixture at that same time with no catalase addition.

The combined mixture of the lactose source 302, alkaline buffer 304, and lactose oxidase enzymes 306, incubate in the mixer/incubator 308 until a target amount of the lactose is enzymatically converted to lactobionic acid before ultimately becoming the lactobionate salt. For a target level of about 100% conversion, the combined mixture may incubate in the mixer/incubator 308 for 6 to 48 hours depending on the incubation conditions. For example, when the combined mixture incubates at a temperature ranging from 25-50° C., a pH ranging between 6 and 7, a dissolved oxygen concentration of at least 3.2 mg O$_2$/L, and the presence of catalase enzymes, the incubation time can range from 8 to 22 hours to reach about 100% enzymatic conversion of lactose to lactobionic acid.

When the enzymatic conversion is complete, the converted combined mixture containing the lactobionate salt may be transferred to a filtration unit 314 that separates the mixture into a filtration retentate 316 and filtration permeate 318. The filtration unit 314 may be an ultrafiltration unit having an ultrafiltration membrane with an exemplary molecular weight cutoff (MWCOs) of five kilodaltons (5 KDa). Molecules and particles of 5 KDa or larger are captured in the filtration retentate 316 while smaller molecules pass through the ultrafiltration membrane as part of the permeate. An exemplary filtration unit 314 may include a spiral-wound ultrafiltration module that has a perforated center conduit through which the permeate 318 can infiltrate and travel, and one or more sheets wrapped around the center conduit. At least one of the sheets is an ultrafiltration membrane that blocks the migration of the retentate while permitting the radial transfer of the liquid permeate to and through the center conduit. The sheets may be made from an organic polymer. Examples of suitable organic polymers include one or more of cellulose acetate, polysulfone, polyvinylidene fluoride, polyethersulfone, polyesters, and polyamide, among other types of organic polymers. Another exemplary filtration unit 314 includes dead-end filtration, where the combined mixture meets a membrane barrier that holds particles larger than the membrane pore size back (i.e., the filtration retentate 316) while permitting smaller particles and liquid to pass through the membrane as the filtration permeate 318.

The filtration retentate 316 includes the lactose oxidase enzymes and, if used, the catalase enzymes. The filtration retentate 316 may also include any larger molecules (e.g., larger than the lactobionate anions) and particulates carried over from the lactose source 302. By filtering these larger molecules and particles upstream of the two-compartment cation bipolar electrodialysis assembly 320, they do not have the opportunity to foul the membranes in the assembly. In some instances, the enzymes recovered in the filtration retentate 316 can be incorporated back into the lactose oxidase enzymes 306 added to the combined mixture in the incubator/mixer 308. In some processes, reincorporation of the recovered enzymes can be done even when the enzymes include a combination of lactose oxidase enzymes and catalase enzymes.

The filtration permeate 318 may be sent directly to the two-compartment cation bipolar electrodialysis assembly 320, or may be diluted to a target concentration of the lactobionate salt. For example, the filtration permeate may be diluted with water to become an aqueous solution of the lactobionate salt having a concentration of 18-22 wt. % (TS basis).

The filtration permeate 318 is input into the two-compartment cation bipolar electrodialysis assembly 320 along with a source of water 322 to convert the lactobionate salts in the permeate into a caustic solution 324 and an aqueous solution of purified lactobionic acid 326. Design and operation details of the two-compartment electrodialysis assembly 320 are provided in FIG. 2 and its accompanying description. The caustic solution 324 includes caustic compounds generated by the bipolar electrodialysis of the lactobionate salts in the filtration permeate. Exemplary caustic compounds include hydroxide compounds (MOH) of the conjugate cation ($M^+$) from the lactobionate salt (MX). For example, caustic compounds may include one or more of sodium hydroxide (NaOH), potassium hydroxide (KOH), ammonium hydroxide ($NH_4OH$), calcium hydroxide ($Ca(OH)_2$), magnesium hydroxide ($Mg(OH)_2$), and zinc hydroxide ($Zn(OH)_2$), among other caustic compounds. Exemplary concentrations of the caustic compound in the caustic solution 324 include 1-5 wt. % (TS basis); 1-4 wt. % (TS basis); 1-3 wt. % (TS basis); and 1-2 wt. % (TS basis). In some embodiments, the caustic solution 324 recovered from the two-compartment electrodialysis assembly 320 may be incorporated back into the alkaline buffer 304 added to the combined mixture in the incubator/mixer 308.

The purified lactobionic acid solution 326, may have lactobionic acid levels of up to 80 wt. %; up to 85 wt. %; up to 90 wt. %; up to 91 wt. %; up to 92 wt. %; up to 93 wt. %; up to 94 wt. %; up to 95 wt. %; up to 96 wt. %; or up to 97 wt. %, among other ranges, of the non-water compounds present in the solution. The purified lactobionic acid solution 326 may have a concentration of total solids that represents greater than 90% conversion of the lactobionate salt to lactobionic acid. For example, a filtration permeate 318 with a lactobionate salt concentration of 18-22 wt. % (TS basis) may produce a purified lactobionic acid solution 326 with a lactobionic acid concentration of 18-20 wt. % (TS basis).

In some embodiments, the purified lactobionic acid solution 326 is packaged and used without further processing. In other embodiments, the purified lactobionic acid solution 326 is transferred to a water separation unit 328, that removes some or all of the water from the lactobionic acid. An exemplary water separation unit 328 is an evaporator that increases the surface area of the solution while heating it to a temperature that rapidly evaporates the water from the lactobionic acid to form a lactobionic acid concentrate 332 or solid product. Another exemplary water separation unit 328 is a spray drier that aerosolizes the purified lactobionic acid solution 326 into a low-humidity, high-temperature chamber that leaves a dry, powdered lactobionic acid product 330.

In some embodiments, even high levels of purity for the purified lactobionic acid solution 326 are desired. In those embodiments, the solution 326 may be transferred to an ion-exchange unit 334 that uses an ion-exchange resin (e.g., cation and/or anion exchange resin) to capture more of the residual conjugate cations ($M^+$) or residual color bodies that may be cationic or anionic in nature. The ultrapurified solution 336 may have exemplary lactobionic acid levels of greater than 97 wt. %; greater than 98 wt. %; greater than 99 wt. %, among other ranges, of the non-water compounds present in the solution.

Exemplary Methods of Making Lactobionic Acid

Figure 4:
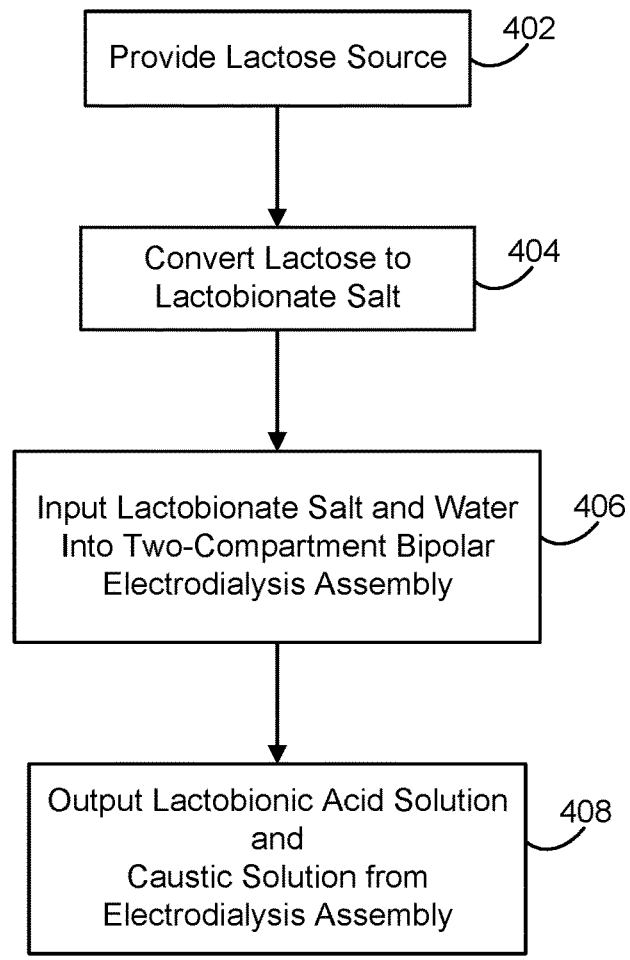
FIG. 4 is a flowchart showing selected steps in a method of making lactobionic acid according to embodiments of the invention.

The two-compartment cation bipolar electrodialysis cells and systems described above are used in the present methods of making purified lactobionic acid products. Those products include aqueous solutions of lactobionic acid, lactobionic acid concentrates, and lactobionic acid solids such as lactobionic acid powders. FIG. 4 shows a flowchart with selected steps in a method 400 of making lactobionic acid according to embodiments of the invention. The method 400 includes providing a lactose source 402. As described elsewhere, exemplary lactose sources may be derived from dairy source such as milk, yogurt, and/or cheese, among other dairy sources. For example, the lactose source may come from a yogurt or cheese-making process that generates as lactose-containing by-product. Depending on the process, the lactose-containing by-product may require further purification (e.g., filtration or crystallization) to make the lactose source, or the lactose-containing by-product may be used directly as the lactose source. Exemplary lactose sources are aqueous solutions or mixtures with a lactose concentration ranging from 30-35 wt. % (TS basis).

Method 400 further includes converting the lactose in the lactose source to a lactobionate salt 404. These conversion methods include an enzymatic oxidation of the lactose sugar to lactobionic acid with a lactose oxidase enzyme. Formulaically, the enzymatic conversion reaction can be represented as:

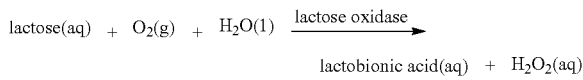

The temperature may be controlled to stay within a target range during the enzymatic conversion. Exemplary temperature ranges include 20-100° C.; 25-85° C.; 20-70° C.; 20-50° C.; 25-60° C.; and 30-50° C., among other temperature ranges for the enzymatic conversion. Temperature control is affected by a cooling and/or heating mechanism thermally coupled to, or incorporated into, the mixer/incubator where the enzymatic reaction takes place.

The pH may also be controlled to stay within a target range during the enzymatic conversion. Exemplary pH ranges include 3 to 10; 4 to 9; 5 to 8; 6 to 8; and 7 to 8, among other pH ranges for the enzymatic conversion. The pH control is affected by the presence of a buffer with the combination of the lactose oxidase enzymes and lactobionate salt. Exemplary buffers include hydroxide compounds (MOH) such as sodium hydroxide (NaOH), potassium hydroxide (KOH), ammonium hydroxide ($NH_4OH$), magnesium hydroxide ($Mg(OH)_2$), calcium hydroxide ($Ca(OH)_2$), and zinc hydroxide ($Zn(OH)_2$), among other compounds. In some embodiments, a single hydroxide compound is used as the buffer, while in other embodiments two or more hydroxide compounds are used. The presence of the hydroxide compound transforms the lactobionic acid (HX), initially formed by the enzymatic conversion of the lactose, into a lactobionate salt (MX) that is converted back to the acid in subsequent steps using two-compartment cation bipolar electrodialysis.

In some embodiments, additional conditions are controlled during the enzymatic conversion of the lactose to lactobionic acid (and ultimately a lactobionate salt). These conditions include the amount of dissolved oxygen ($O_2$(aq)) in the aqueous mixture where the conversion takes place. The formula above for the enzymatic conversion indicates, oxygen is a required reactant for the conversion, so an increased concentration of dissolved oxygen in the conversion medium can increase the conversion rate. Exemplary levels of dissolved oxygen in the aqueous mixture include ranges of at least 3.2 mg $O_2$/L; 5 to 200 mg $O_2$/L; and 7 to 30 mg $O_2$/L; among other ranges. Increasing the dissolved oxygen level can be affected both by physically transporting more oxygen $O_2$(aq) into the aqueous mixture, as well as adding a catalase enzyme to the mixture that catalyzes the conversion of the peroxide product ($H_2O_2$(aq)) back into water ($H_2O$(l)) and more oxygen $O_2$(aq). As noted elsewhere, exemplary techniques to transport oxygen into the aqueous mixture include pumping air or purified oxygen into the mixture. In some embodiments, the oxygen level in the aqueous mixture is monitored during the enzymatic conversion, and additional oxygen is transported into the mixture when the concentration of dissolved oxygen falls below a threshold level (e.g., 3.2 mg $O_2$/L). In other embodiments, the oxygen level in the mixture is not monitored, and oxygen is transported into the mixture a predetermined rate throughout the enzymatic conversion process.

The enzymatic conversion is completed when a target yield of lactobionate salts are converted from the staring lactose. Exemplary target yields include 60 mol. % or more; 70 mol. % or more; 80 mol. % or more; 90 mol. % or more; 95 mol. % or more; and 99 mol. % or more, among other target yields. Under controlled conversion conditions, conversion times can be used as a proxy for reaching the target yield. Exemplary conversion time ranges include 6 to 48 hours; 8-30 hours; 10-22 hours; and 12-20 hours; among other conversion time ranges.

The method 400 further includes inputting the aqueous mixture of lactobionate salt, and an additional source of water, into a two-compartment cation bipolar electrodialysis assembly 406. As noted elsewhere, the aqueous mixture (or solution) of lactobionate salt forms a stream in one of the compartments of the assembly that is transformed from primarily containing the lactobionate salt to primarily containing lactobionic acid (i.e., a purified lactobionic acid stream). The additional water forms an independent caustic stream in the other compartment of the assembly that is transformed from primarily pure water to the caustic stream that has absorbed caustic compounds (e.g., hydroxide compounds) from the conjugate cations ($M^+$) and hydroxyl groups ($OH^-$) from the membranes that define the borders of the compartment. During the operation of the two-compartment cation bipolar electrodialysis assembly, the conjugate cations ($M^+$) cross a cation exchange membrane from the lactobionic acid stream to the caustic stream, while the lactobionate anions ($X^-$) remain in the same stream (i.e., the lactobionic acid stream) without crossing a membrane, which significantly reduces membrane fouling caused by the lactobionate anions ($X^-$). Exemplary flow rates for the aqueous mixture of lactobionate salt include 5,000 to 15,000 lbs of the mixture per hour (e.g., 11,000 lbs/hour). Exemplary flow rates for the additional source of water include 2500 to 15,000 pounds of water per hour (e.g., 10,300 lbs/hour). Exemplary flow rates for the output purified lactobionic acid stream include ranges of 2500 to 15,000 lbs per hour at a 2 wt. % (TS) concentration (e.g., 10,300 lbs/hour).

The method 400 also includes outputting a lactobionic acid solution and caustic solution from their respective streams in the two-compartment cation bipolar electrodialysis assembly 408. Because of the reduced level of membrane fouling, the output rates from the assembly remain substantially constant over long periods of time. For example, after five continuous hours of use, the two-compartment cation bipolar electrodialysis assembly may have an output rate for the lactobionic acid solution that is at least 80% of the initial rate; at least 85% of the initial rate; at least 90% of the initial rate; at least 92% of the initial rate; at least 95% of the initial rate; or at least 99% of the initial rate. Exemplary flow rates for the output lactobionic acid solution may include 2,500 lbs/hour to 10,000 lbs/hour (e.g., 3,500 lbs/hour).

The lactobionic acid solution output from the assembly may have lactobionic acid levels of up to 80 wt. %; up to 85 wt. %; up to 90 wt. %; up to 91 wt. %; up to 92 wt. %; up to 93 wt. %; up to 94 wt. %; up to 95 wt. %; up to 96 wt. %; or up to 97 wt. %, among other ranges, of the non-water compounds present in the solution. The lactobionic acid solution may have a concentration of total solids that represents greater than 90% conversion of the lactobionate salt to lactobionic acid. For example, the starting aqueous solution of lactobionate salt input into the assembly may have a concentration of 18-22 wt. % (TS basis), and the output lactobionic acid solution may have a lactobionic acid concentration of 18-20 wt. % (TS basis).

Figure 5:
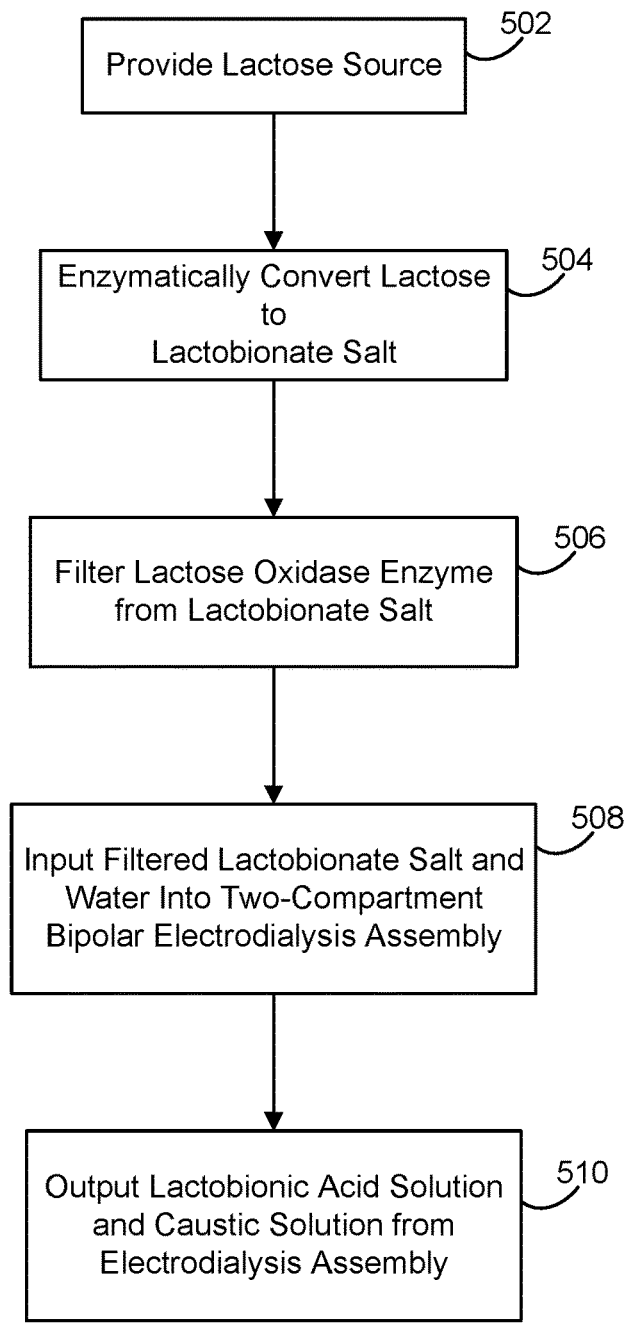
FIG. 5 is a flowchart showing selected steps in a method of making lactobionic acid according to additional embodiments of the invention.

The reduced rates of membrane fouling in the present methods can be reduced further by removing the enzymes and other larger-sized compounds and particles in the aqueous mixture of lactobionate salt that is input to the two-compartment cation bipolar electrodialysis assembly. FIG. 5 is a flowchart that shows selected steps in a method 500 of making lactobionic acid that includes enzyme removal from an aqueous solution of the lactobionate salt that is subsequently input into the electrodialysis assembly. The method 500 includes providing a lactose source 502. As described above, the lactose source may be an aqueous lactose solution with a lactose concentration ranging from 30-35 wt. % (TS basis).

The lactose source is combined with lactose oxidase enzymes and a buffer to form a combined mixture where the lactose is enzymatically converted to lactobionic acid, and ultimately a lactobionate salt 504. In some embodiments catalase enzymes are also added to the combined mixture to provide more oxygen for lactose conversion by enzymatically converting the hydrogen product of the lactose conversion back into water and oxygen ($O_2$). The enzymatic conversion of the lactose to lactobionic acid is completed when a target percentage of the lactose has been converted. Exemplary percentages include 60 mol % of more; 70 mol. % or more; 80 mol. % or more; 90 mol. % or more; 95 mol. % or more; and 99 mol. % or more, among other target conversion percentages. Under controlled conversion conditions, conversion times can be used as a proxy for reaching the target percentage of lactose conversion. Exemplary conversion time ranges include 6 to 48 hours; 8-30 hours; 10-22 hours; and 12-20 hours; among other conversion time ranges.

As noted above, method 500 includes filtering the lactose oxidase enzymes from the aqueous lactobionate salt produced by the enzymatic conversion process 506. The filtration process may include transferring the enzyme-containing mixture to a filtration unit that separates the mixture into (i) an enzyme-containing retentate and (ii) a lactobionate salt-containing permeate. The permeate lacks the enzymes and other larger-sized compounds and particles that are captured in the retentate. This further reduces the fouling caused by the aqueous solution of the lactobionate salt as it flows through the two-compartment cation bipolar electrodialysis assembly.

Exemplary filtration processes include ultrafiltration of the enzyme-containing aqueous lactobionate salt mixture with an ultrafiltration membrane having a molecular weight cutoff (MWCOs) of five kilodaltons (5 KDa). Molecules and particles of 5 KDa or larger are captured in the retentate while smaller molecules pass through the ultrafiltration membrane as part of the permeate. Exemplary ultrafiltration units include a spiral-wound ultrafiltration module that has a perforated center conduit through which the permeate can infiltrate and travel, and one or more sheets wrapped around the center conduit. At least one of the sheets is an ultrafiltration membrane that blocks the migration of the retentate while permitting the radial transfer of the liquid permeate to and through the center conduit. The sheets may be made from an organic polymer. Examples of suitable organic polymers include one or more of cellulose acetate, polysulfone, polyvinylidene fluoride, polyethersulfone, polyesters, and polyamide, among other types of organic polymers. Another exemplary filtration unit includes dead-end filtration, where the combined mixture meets a membrane barrier that holds particles larger than the membrane pore size back (i.e., the filtration retentate) while permitting smaller particles and liquid to pass through the membrane as the filtration permeate.

The filtered aqueous solution of the lactobionate salt and an additional source of water are input into the two-compartment cation bipolar electrodialysis assembly 508. In some embodiments, the filtered aqueous solution of the lactobionate salt is input directly to the assembly without further processing. In other embodiments, the filtered aqueous solution of the lactobionate salt undergoes additional processing before being input to the assembly. For example, water may be added to the initial filtration permeate to reduce the percentage of total solids in the permeate. Exemplary concentration ranges for the diluted aqueous solution of the lactobionate salt include 15-25 wt. % (TS Basis); and 18-22 wt. % (TS Basis), among other ranges.

The two-compartment cation bipolar electrodialysis assembly outputs a purified lactobionic acid solution and a caustic solution 510. The absence of enzymes and other larger-sized compounds and particles during the conversion of the lactobionate salts to lactobionic acid in the assembly permits longer assembly run times before cleaning and maintenance is required. For example, after five continuous hours of use, the two-compartment cation bipolar electrodialysis assembly may have an output rate for the lactobionic acid solution that is at least 85% of the initial rate; at least 90% of the initial rate; at least 92% of the initial rate; at least 95% of the initial rate; at least 97% of the initial rate; or at least 99% of the initial rate. Exemplary flow rates for the output lactobionic acid solution may include 2,500 lbs/hour to 10,000 lbs/hour (e.g., 3,500 lbs/hour).

Figure 6:
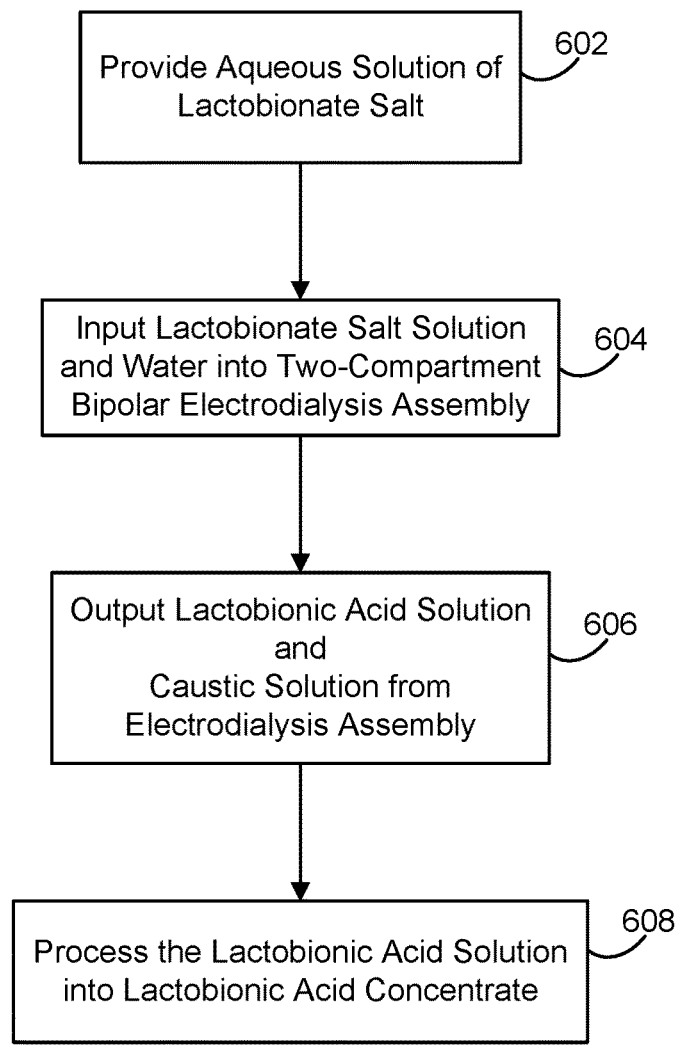
FIG. 6 is a flowchart showing selected steps in a method of making a lactobionic acid concentrate according to embodiments of the invention.

The lactobionic acid solution produced by methods 400 and 500 may be used directly in other applications (not shown) or may be further processed. For example, FIG. 6 shows selected steps in a method 600 of making a lactobionic acid concentrate from a purified lactobionic acid solution. The method 600 includes providing an aqueous solution of a lactobionate salt 602. The lactobionate salt solution may be provided from the enzymatic conversion of lactose to lactobionic acid (and ultimately a lactobionate salt), as described above.

The aqueous lactobionate salt solution and a separate source of water may be input into a two-compartment cation bipolar electrodialysis assembly 604. The assembly converts the input aqueous lactobionate salt solution into a lactobionic acid solution, and converts the input water source into a caustic solution. Both the lactobionic acid and caustic solutions are output from the assembly 606.

Method 600 further includes processing the lactobionic acid solution output from the two-compartment cation bipolar electrodialysis assembly into a lactobionic acid concentrate 608. The processing may include inputting the lactobionic acid solution into an evaporator unit that heats and increases the surface area to volume ratio of the solution to remove a portion of the water. The evaporator unit concentrates the lactobionic acid solution until a target concentration (e.g., total solid percentage) is reached in the lactobionic acid concentrate. Exemplary target concentration ranges include 20-95 wt. % (TS basis); 30-95 wt. % (TS basis); 40-95 wt. % (TS basis); 50-95 wt. % (TS basis); 60-95 wt. % (TS basis); 70-95 wt. % (TS basis); 80-95 wt. % (TS basis); 90-95 wt. % (TS basis); and 35-99 wt. % (TS basis), among other exemplary ranges.

Figure 7:
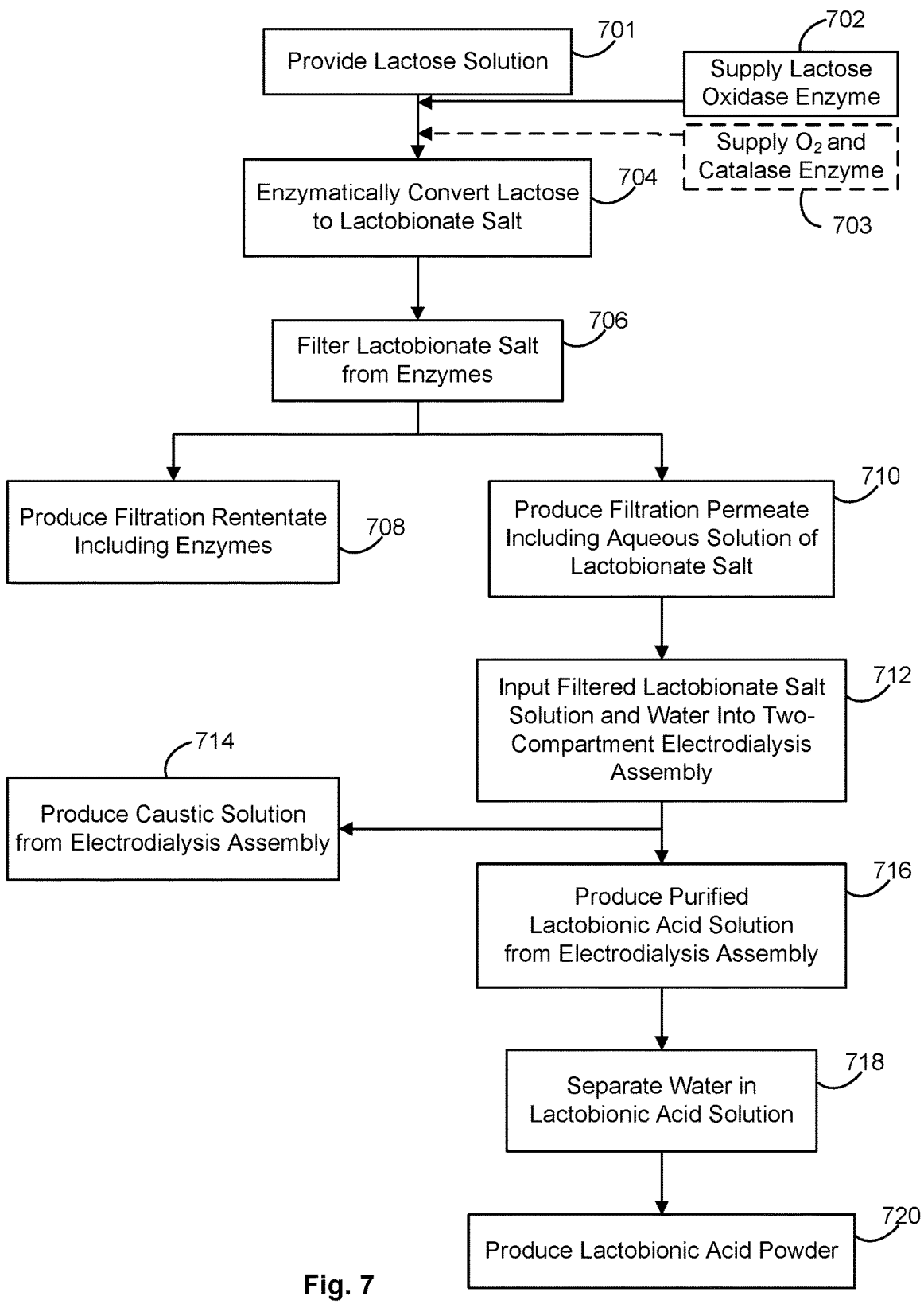
FIG. 7 is a flowchart showing selected steps in a method of making a lactobionic acid powder according to embodiments of the invention.

Lactobionic acid powders may also be made for the purified aqueous solutions of lactobionic acid. FIG. 7 is a flowchart that shows selective steps in a method 700 of making lactobionic acid powders according to embodiments of the invention. The method 700 includes providing a lactose solution 701 that supplies the lactose for enzymatic conversion into lactobionic acid, and ultimately a lactobionate salt. As noted elsewhere, exemplary lactose solutions have a lactose concentration ranging from 30-35 wt. % (TS basis). The lactose is enzymatically converted to lactobionic acid, and ultimately a lactobionate salt 704. The enzymatic conversion may occur in a combined aqueous mixture that includes the lactose, lactose oxidase enzymes, and a buffer that keeps the pH in a target range during the conversion. The lactose oxidase enzymes can be supplied to the lactose solution 702. In some embodiments, oxygen ($O_2(g)$) and/or catalase enzyme may also be added to the combined mixture 703. The oxygen and/or catalase may be added concurrently with the lactose oxidase enzymes, or may be added after the catalytic conversion of the lactose has commenced.

When the conversion of the lactose is completed, the aqueous mixture containing the enzymes and lactobionate salt may be filtered 706 to separate the enzymes, and other larger-sized compounds and particles, from a filtered aqueous solution of the lactobionate salt. The filtration produces a filtration retentate that includes the enzymes 708, including the lactose oxidase enzymes, and catalase enzymes if present in the mixture. The filtration also produces the aqueous solution of the lactobionate salt 710. In some embodiments (not shown) the aqueous lactobionate salt solution may be further processed, such as by adjusting the lactobionate salt concentration to a target value (e.g., 18-22 wt. % (TS Basis) of lactobionate salts).

The filtered lactobionate salt solution and additional water are input into a two-compartment cation bipolar electrodialysis assembly 712. The assembly converts the lactobionate salt into lactobionic acid and produces two output solutions: A caustic solution is produced by the assembly 714 from the accumulation of caustic compounds (e.g., hydroxide compounds) in the additional water stream input to the assembly. A purified lactobionic acid solution produced by the assembly 716 from the filtered lactobionate salt solution stream input to the assembly. In some embodiments, the caustic compounds in the caustic solution are incorporated back into the buffer used in the combined mixture where the enzymatic lactose conversion occurs. In other embodiments, the caustic solution is discarded.

The purified lactobionic acid solution output from the two-compartment cation bipolar electrodialysis assembly is transferred to a spray dryer to remove the water in the solution 718. The spray drier sends the purified lactobionic acid solution through one or more pressurized nozzles that aerosolize the solution into a hot, dry chamber that rapidly evaporates the water from the aerosolized droplets to leave behind particulates of the lactobionic acid. The particulates accumulate in the bottom of the chamber to produce a lactobionic acid powder 720. The lactobionic acid powder may be further processed, packaged, and/or transported to another location.

EXPERIMENTAL

In the experimental examples discussed below, aqueous streams of lactobionate salts (i.e., salt streams) are purified using three different configurations of electrodialysis assemblies. The first assembly is a conventional electrodialysis assembly that uses a combination of cation and anion exchange membranes to separate the lactobionate salt into separate streams for the conjugate cation and lactobionate anion. The second assembly is a three-compartment bipolar electrodialysis assembly that uses a bipolar membrane in combination with cation and anion exchange membranes to separate the lactobionate salt into three streams, one of which is the purified lactobionic acid. The third assembly is a two-compartment cation bipolar electrodialysis assembly that represents an exemplary embodiment of the invention. The assembly includes a bipolar membrane and cation exchange membrane that separates the stream of lactobionate salt into a purified stream of lactobionic acid and a caustic stream containing the hydroxide of the conjugate cation from the lactobionate salt. In Examples 3 and 4 below, the two-compartment cation bipolar membrane assembly is used to purify streams of potassium lactobionate and ammonium lactobionate salts, respectively. As shown through these comparative examples, the fouling of the membranes in the first and second assemblies, caused by the difficult passage of the large lactobionate anion through these membranes, significantly limits their productivity. In contrast, the two-compartment cation bipolar electrodialysis assembly, which does not try to pass the lactobionate anion through a membrane, can operate at full productivity for several hours without experiencing the deleterious effects of membrane fouling.

The examples below describe the production of a lactobionic acid composition that is derived from a lactobionate salt, which in turn is made from lactose. The examples start with an aqueous lactose solution concentrated to 30-35 wt. % total solids. An alkaline buffer such as potassium hydroxide or ammonium hydroxide is added to the lactose solution to keep the pH in a range of 6 to 8 during the enzymatic hydrolysis of the lactose. Lactose oxidase is added to the buffered lactose solution to enzymatically convert the lactose into the lactobionate salt. The enzymatic conversion is run to completion to produce a solution of a lactobionate salt (e.g., potassium or ammonium lactobionate) with the same 30-35 wt. % total solids. Sodium lactobionate has not been trialed in these experiments but should provide similar results as potassium lactobionate since both sodium and potassium ions are monovalent cations.

The enzyme-containing lactobionate salt solution is ultrafiltered using a membrane having a molecular weight cutoff of 5 kDa to remove the enzymes from the filtered permeate of lactobionate salt solution. As noted above, the removal of the enzymes from the lactobionate salt solution reduces the rate of fouling of the membranes in the electrodialysis assembly. The filtered (i.e., enzyme-depleted) lactobionate salt solution is diluted with water until reaching a 22 wt. % total solids concentration.

The diluted lactobionate salt solution is fed to a two-compartment electrodialysis assembly that includes a ten-cell stack configuration having a stainless-steel cathode electrode and a platinum/titanium anode electrode. The membranes in the assembly are separated by flow distribution gaskets (spacers) which were arranged to give one cell unit that included combinations of a cation exchange membrane, an anion exchange membrane (for three-component assemblies), and a bipolar membrane.

The diluted lactobionate salt solutions were circulated through the assembly for 5 min before the current was switched on to condition the membranes in the assembly, as well as eliminate any possible air bubbles. Experiments were targeted to achieve feed pH≤2.0.

Example 1—Production of Lactobionic Acid Using Conventional Electrodialysis

In Example 1, two types of ion-exchange membranes were used: (i) A cation-exchange membrane which only allows cations to be transported through the membrane, and (ii) an anion-exchange membrane which only allows anions to be transported through the membrane. The cation was potassium and the anion as lactobionate ion. Alternating cation (CR61HMP) and anion-exchange (AR103) membranes were assembled to form diluate (caustic) and concentrate (acid) compartments in the electrodialysis stack. The initial caustic stream (water) and the salt stream (lactobionate salt at 22% total solids) each had a 4 liters volume, with pHs of 7.8 and 4.6, respectively. The applied voltage on the assembly's electrodes was initially 29.1 volts (V), and remained constant throughout the batch run through the electrodialysis assembly. The direct current amperage started at 2.40 amps (A), and dropped in half after 10 min of the batch run, as shown in Table 1:

TABLE 1

Experimental Results for Production of Lactobionic Acid with Conventional Electrodialysis

| | | | Stream | | | | | | | |
|---|---|---|---|---|---|---|---|---|---|---|
| | | | Caustic | | | | Salt | | | |
| Time (min) | Voltage (volt) | Amp (Amp) | Conductivity (mS/cm) | pH | Flow rate (LPM) | Pressure (PSI) | Conductivity (mS/cm) | pH | Flow rate (LPM) | Pressure (PSI) |
| 0.00 | 29.10 | 2.40 | 0.14 | 7.79 | 2.50 | 3.00 | 34.75 | 4.56 | 2.50 | 3.00 |
| 10.00 | 29.10 | 1.21 | 3.41 | 8.20 | 0.50 | 5.00 | 20.06 | 4.46 | 0.50 | 5.00 |

The flow rate for the streams declined five-fold, from 2.50 LPM to 0.50 LPM, during the 10 min batch run despite a constant increase in feed pump pressure from 3 PSI to 5 PSI. The decrease in amperage and flow rate parameters indicated membrane fouling. When investigated, anion exchange membranes were severely fouled with a crystalline material adhering to the membrane. Composition testing of the crystalline material revealed it to be the lactobionate salt precipitated from the lactobionate salt feed stream.

Example 2—Production of Lactobionic Acid with Three-Compartment Bipolar Electrodialysis In this example, a three-compartment bipolar electrodialysis assembly was used to purify a potassium lactobionate solution. The assembly used three types of membranes in each cell: (i) a cation exchange membrane (CR61HMP), (ii) anion exchange membrane (AR103), and (iii) bipolar membrane (BP-1). Ten cells were then serially arranged to form three flow channels (i.e., compartments) in a ten-cell stack-pack. The three compartments in the assembly were connected to an external reservoir to allow continuous recirculation of three separate streams of materials: (i) a salt stream (i.e., aqueous potassium lactobionate), (ii) a caustic stream (i.e., aqueous potassium hydroxide), and (iii) an acid stream (i.e., purified aqueous lactobionic acid). The streams were circulated using centrifugal pumps, and flow rates were measured by means of flow-meters. After the streams circulated for five minutes, current was supplied to the assembly. Similar to example 1, the applied voltage was initially at 30 V but after 10 min, it was set to 40 V to speed up the ion removal. The direct current amperage started at 0.92 A, and was gradually incremented until reaching a peak of 1.22 A. Table 2 shows selected characteristics of the three material streams between their initial introduction to the three-compartment bipolar electrodialysis assembly and after 195 minutes of circulation through the assembly:

TABLE 2

Experimental Results for Production of Lactobionic Acid with Three-Compartment Bipolar Electrodialysis

| Time (min) | Voltage (volt) | Amp (Amp) | Acid | | | | Salt | | | | Caustic | | | |
|---|---|---|---|---|---|---|---|---|---|---|---|---|---|---|
| | | | Conductivity (mS/cm) | pH | Flow rate (LPM) | Pressure (PSI) | Conductivity (mS/cm) | pH | Flow rate (LPM) | Pressure (PSI) | Conductivity (mS/cm) | pH | Flow rate (LPM) | Pressure (PSI) |
| 0.00 | 30.00 | 0.92 | 0.29 | 7.50 | 2.25 | 3.00 | 5.41 | 4.60 | 2.00 | 3.00 | 0.30 | 7.50 | 1.90 | 3.00 |
| 195.00 | 40.00 | 1.22 | 1.89 | 1.79 | 2.50 | 5.00 | 4.18 | 4.41 | 1.50 | 5.60 | 31.20 | 12.71 | 2.00 | 3.00 |

After the three material streams were circulating for 1 hour, the feed flow-rate declined despite an increase in process and pump pressure, which indicated membrane fouling. When investigated, anion exchange membranes were fouled due to the large molecular weight of lactobionate ions being impervious to the membrane. Repeated the process by using different anion exchange membrane (AR204) with increased ion exchange capacity (2.4 vs 2.2 meq/dry g resin) with reduced thickness (0.5 mm vs 0.6 mm) in light of minimizing resistance to ion mobility but had the same fouling issue as with AR103.

Example 3—Production of Lactobionic Acid from Potassium Lactobionate with Two-Compartment Cation Bipolar Electrodialysis In Example 3, a two-compartment cation bipolar electrodialysis assembly was used to purify a potassium lactobionate solution. The assembly used CR61HMP cation exchange membranes to selectively permeate cations from the potassium lactobionate feed, and BP-1 bipolar membranes to split water into hydrogen and hydroxyl ions. The membranes formed two flow channels (i.e., compartments) to guide two separate material streams through the assembly: (i) a salt stream of an aqueous potassium lactobionate solution (22 wt. % total solids), and (ii) a caustic stream of aqueous potassium hydroxide. The salt stream was recirculated through the assembly in a flow channel that permitted the exchange of potassium ions in the stream with hydrogen ions generated by the bipolar membrane. While the potassium ions crossed from the salt stream to the caustic stream through the cation exchange membrane, the lactobionate ions remained in the purifying salt stream and did not cross a membrane in the assembly. Other settings of this batch were comparable to Example 1, however, there was no indication of membrane fouling. Table 3 shows selected characteristics of the two streams after running them through the two-compartment cation bipolar electrodialysis assembly for four hours:

TABLE 3

Experimental Results for Production of Lactobionic Acid from Potassium Lactobionate with Two-Compartment Cation Bipolar Electrodialysis

| | | | Stream | | | | | | | |
|---|---|---|---|---|---|---|---|---|---|---|
| | | | Caustic | | | | Salt (Feed) | | | |
| Time (min) | Voltage (volt) | Amp (Amp) | Conductivity (mS/cm) | pH | Flow rate (LPM) | Pressure (PSI) | Conductivity (mS/cm) | pH | Flow rate (LPM) | Pressure (PSI) |
| 0.00 | 39.90 | 1.79 | 0.55 | 6.98 | 2.00 | 2.50 | 31.43 | 6.16 | 2.00 | 3.50 |
| 240 | 39.90 | 7.60 | 3.42 | 10.94 | 2.00 | 2.50 | 1.82 | 1.83 | 2.00 | 3.00 |

As shown in Table 3, the system successfully ran for 4 hours (240 min) and cations were freely moving from the salt to the caustic stream as depicted by change in pH of the streams. During this run, there was significant increase in cation removal rate and demineralization was completed when feed pH reached to 1.83. In this configuration, negatively-charged lactobionate anions combined with positively-charged hydrogen ions, generated from the bipolar membrane, to form lactobionic acid that is recirculated back to salt stream after removal of the potassium cation to the caustic stream as potassium hydroxide. This resulted in producing purified lactobionic acid (≥95% pure) at the end of the electrodialysis process. If further purification is desired (100%), purified stream from electrodialysis can be treated with suitable ion exchange resin to remove remaining ions. This combination (electrodialysis and ion exchange resin) is more favorable than using ion exchange resin alone as the first part of electrodialysis removes 97-98% of ions (and only need small scale ion exchange resin to remove remaining 2-3% ions) that provides sustainability due to no chemical regeneration requirement. This makes the combination process more cost effective as well as more environmentally friendly compared to processes that rely solely on ion exchange resins.

Example 4—Production of Lactobionic Acid from Ammonium Lactobionate with Two-Compartment Cation Bipolar Electrodialysis In Example 4, a two-compartment cation bipolar electrodialysis assembly was used to purify an ammonium lactobionate solution. Similar to Example 3, the assembly used CR61HMP cation exchange membranes to selectively permeate cations from the potassium lactobionate feed, and BP-1 bipolar membranes to split water into hydrogen and hydroxyl ions. The membranes formed two flow channels (i.e., compartments) to guide two separate material streams through the assembly: (i) a salt stream of an aqueous ammonium lactobionate solution (22 wt. % total solids), and (ii) a caustic stream of aqueous ammonium hydroxide. The salt stream was recirculated through the assembly in a flow channel that permitted the exchange of ammonium ions in the stream with hydrogen ions generated by the bipolar membrane. While the ammonium ions crossed from the salt stream to the caustic stream through the cation exchange membrane, the lactobionate ions remained in the purifying salt stream and did not cross a membrane in the assembly. Other settings of this batch were comparable to Examples 1 and 3. Table 4 shows selected characteristics of the two streams after running them through the two-compartment cation bipolar electrodialysis assembly for five hours:

TABLE 4

Experimental Results for Production of Lactobionic Acid from Ammonium Lactobionate with Two-Compartment Cation Bipolar Electrodialysis

| | | | Stream | | | | | | | |
|---|---|---|---|---|---|---|---|---|---|---|
| | | | Caustic (Water) | | | | Salt (Feed) | | | |
| Time (min) | Voltage (volt) | Amp (Amp) | Conductivity (mS/cm) | pH | Flow rate (LPM) | Pressure (PSI) | Conductivity (mS/cm) | pH | Flow rate (LPM) | Pressure (PSI) |
| 0.00 | 40.50 | 0.00 | 0.18 | 8.79 | 2.00 | 3.50 | 32.39 | 5.78 | 2.00 | 3.50 |
| 300.00 | 40.50 | 3.14 | 2.45 | 10.82 | 2.00 | 3.50 | 2.34 | 2.05 | 2.00 | 3.50 |

As shown in Table 4, the system successfully ran for 5 hours (300 min) and cations were freely moving from feed to water stream as depicted by change in pH of both feed and caustic stream. During this run, there was significant increase in cation removal rate and demineralization was completed when feed pH reached to 2.05. In this configuration, negatively-charged lactobionate anions combined with positively-charged hydrogen ions, generated from the bipolar membrane, to form lactobionic acid that is recirculated back to salt stream after removal of the ammonium cation to the caustic stream as ammonium hydroxide. This resulted in producing purified lactobionic acid at the end of the electrodialysis process. After going through electrodialysis, lactobionic acid was lighter in appearance as compared to its salt counterpart. We compared the color of two streams (i.e. lactobionate salt and lactobionic acid) and discovered yellowness was reduced by ~30%. Further purity and decolorization was completed by using anion exchange resin and activated carbon filters.

The purified lactobionic acid as depicted in Examples 3 and 4 was then passed through an ion-exchange column for decolorization and the caustic streams (i.e., potassium hydroxide or ammonium hydroxide from Examples 3 and 4, respectively) can be recycled in reaction set up to convert lactose to lactobionate salt. Decolorization of lactobionic acid was completed with Sepabeads SP700 resin (Mitsubishi Chemical) in column chromatography with 19 cm deep, 2 cm diameter glass column. The feed (lactobionic acid) was loaded from top to flow over the resin and fed through column by gravity at ~60° F. temperature. The flow-rate was at 6 BV/hr and decolorization was completed by reducing yellowness (hunter colorimeter b* value) to ~65% from starting to finish. After decolorization, the lactobionic acid is evaporated to increase total solids from ~20% (at pH<2.0) to >=70% syrup. The evaporated lactobionic acid syrup can be optionally spray dried to achieve powder with 2-5% moisture.

From Examples 3 and 4, lactobionic acid was generated from lactobionate salt and the purity was dependent on ion removal rate. Table 5 compares the compositions of the initial salt streams and final products in Examples 3 and 4:

TABLE 5

Purity Characteristics of Lactobionic Acid Made from Potassium and Ammonium Lactobionate Purified with Two-Compartment Cation Bipolar Electrodialysis

| Parameters | KLB Feed | LBA | $NH_4LB$ Feed | LBA |
|---|---|---|---|---|
| Total Solids % | 21.56 | 19.01 | 23.15 | 21.46 |
| Ash % | 3.268 | 0.119 | 0.06 | 0.04 |
| Total Protein % | 0.024 | 0.020 | 5.03 | ND |
| Non Protein Nitrogen % | 0.023 | 0.017 | 5.00 | 0.108 |
| Potassium % | 1.20 | 0.0490 | 0.0090 | 0.0023 |
| Sodium % | 0.0109 | 0.0034 | 0.0066 | 0.0044 |
| Calcium % | 0.0033 | 0.0011 | 0.0032 | 0.0007 |
| Magnesium % | 0.0005 | 0.0006 | 0.0006 | 0.0002 |
| Chloride % | 0.0220 | 0.0101 | 0.0259 | 0.0111 |

In Table 5 above, criteria for measuring lactobionic acid purity is different based on the type of feed or lactobionate salt. When potassium lactobionate is feed material, the purity of finished lactobionic acid is measured by removal rate of ash and/or potassium ion, however, when ammonium lactobionate is used as feed material, the measurement criterion is removal of non-protein nitrogen as highlighted in above table.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the ion" includes reference to one or more ions and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A method of making lactobionic acid from a lactobionate salt, the method comprising:
    passing the lactobionate salt through an electrodialysis assembly comprising at least one two-compartment cation bipolar membrane cell, wherein the electrodialysis assembly separates the lactobionate salt into a caustic compound and the lactobionic acid, further wherein a lactobionate ion does not cross an ion exchange membrane in the electrodialysis assembly to form the lactobionic acid, and also wherein the method significantly reduces or eliminates membrane fouling.

2. The method of claim 1, wherein the lactobionate salt is provided by:
    converting lactose to the lactobionate salt with a lactose oxidase enzyme; and
    filtering the lactose oxidase enzyme from the lactobionate salt so that the lactobionate salt includes less than 0.02 wt. %, on a dry basis, of the lactose oxidase enzyme.

3. The method of claim 1, wherein the lactobionate salt is provided by:
    mixing a powder of the lactobionate salt with water.

4. The method of claim 3, wherein the mixture of the lactobionate salt with the water consists essentially of the lactobionate salt and the water.

5. The method of claim 3, wherein the mixture of the lactobionate salt with the water has a total solids concentration of 20% to 25%.

6. The method of claim 1, wherein the lactobionate salt comprises sodium lactobionate, potassium lactobionate, ammonium lactobionate, calcium lactobionate, magnesium lactobionate, or zinc lactobionate.

7. The method of claim 1, wherein the two-compartment biopolymer membrane cell includes a bipolar membrane that dissociates water molecules into hydrogen ions and hydroxyl ions upon application of an electric field to the bipolar membrane.

8. The method of claim 7, wherein the bipolar membrane comprises a first polymer layer that is selectively permeable to the hydrogen ions and a second polymer layer that is selectively permeable to the hydroxyl ions.

9. The method of claim 1, wherein the two-compartment bipolar membrane cell further includes a cation exchange membrane.

10. The method of claim 9, wherein the cation exchange membrane forms separate flow channels in the two-compartment bipolar membrane cell for (i) the caustic compound and (ii) the lactobionic acid.

11. The method of claim 10, wherein the lactobionate salt is converted into the lactobionic acid in the lactobionic acid flow channel without crossing the cation exchange membrane.

12. The method of claim 11, wherein the lactobionic acid is formed by combining a lactobionate ion from the lactobionate salt with a hydrogen ion generated by a bipolar membrane in the two-component bipolar membrane cell.

13. The method of claim 10, wherein a conjugate cation in the lactobionate salt crosses the cation exchange membrane to form the caustic compound in the caustic compound flow channel.

14. The method of claim 10, wherein the conjugate cation combines with a hydroxyl ion to form the caustic compound.

15. The method of claim 14, wherein the hydroxyl ion is formed by dissociation of a water molecule in a bipolar membrane of the two-component bipolar membrane cell.

16. The method of claim 13, wherein the conjugate cation comprises a sodium ion, a potassium ion, an ammonium ion, a calcium ion, a magnesium ion, or a zinc ion.

17. A method of making a lactobionic acid concentrate from a lactobionate salt, the method comprising:
passing an aqueous lactobionate salt solution through an electrodialysis assembly comprising at least one two-compartment bipolar membrane cell, wherein the electrodialysis assembly separates the aqueous lactobionate salt solution into a caustic compound solution and a lactobionic acid solution, further wherein a lactobionate ion does not cross an ion exchange membrane in the electrodialysis assembly to form the lactobionic acid solution, and also wherein the method significantly reduces or eliminates membrane fouling; and
evaporating a portion of water from the lactobionic acid solution to form the lactobionic acid concentrate, wherein the lactobionic acid concentrate has a total solids content of at least 10%.

18. The method of claim 17, wherein the lactobionic acid solution is 95 wt. % or more lactobionic acid on a dry basis.

19. The method of claim 17, wherein the lactobionic acid solution is 97 wt. % or more lactobionic acid on a dry basis.

20. A method of making lactobionic acid from a lactobionate salt, the method comprising:
converting lactose to the lactobionate salt with a lactose oxidase enzyme;
filtering the lactose oxidase enzyme from the lactobionate salt so that the lactobionate salt includes less than 0.02 wt. %, on a dry basis, of the lactose oxidase enzyme;
passing the filtered lactobionate salt through an electrodialysis assembly comprising at least one two-compartment cation bipolar membrane cell, wherein the electrodialysis assembly separates the lactobionate salt into a caustic compound and the lactobionic acid, further wherein a lactobionate ion does not cross an ion exchange membrane in the electrodialysis assembly to form the lactobionic acid, and also wherein the lactobionate salt solution comprises greater than or about 33 ppm calcium.

21. The method of claim 20, wherein the lactobionate salt comprises sodium lactobionate, potassium lactobionate, ammonium lactobionate, calcium lactobionate, magnesium lactobionate, or zinc lactobionate.

22. The method of claim 20, wherein the caustic compound comprises sodium hydroxide, potassium hydroxide, ammonium hydroxide, calcium hydroxide, magnesium hydroxide, or zinc hydroxide.

* * * * *